US006981426B2

(12) United States Patent
Wang et al.

(10) Patent No.: US 6,981,426 B2
(45) Date of Patent: Jan. 3, 2006

(54) METHOD AND APPARATUS TO MEASURE GAS AMOUNTS ADSORBED ON A POWDER SAMPLE

(75) Inventors: Dezheng Wang, Beijing (CN); Fei Wei, Beijing (CN); Jinfu Wang, Beijing (CN)

(73) Assignee: Tsinghua University, Beijing (CN)

( * ) Notice: Subject to any disclaimer, the term of this patent is extended or adjusted under 35 U.S.C. 154(b) by 34 days.

(21) Appl. No.: 10/736,829

(22) Filed: Dec. 15, 2003

(65) Prior Publication Data

US 2004/0134258 A1    Jul. 15, 2004

(30) Foreign Application Priority Data

Jan. 10, 2003  (CN) .................................... 3100285
Nov. 14, 2003  (CN) .......................... 200310113533

(51) Int. Cl.
    *G01N 15/08* (2006.01)

(52) U.S. Cl. ........................................ 73/865.5; 73/38

(58) Field of Classification Search ................. 73/38, 73/865.5
     See application file for complete search history.

(56) References Cited

U.S. PATENT DOCUMENTS 5,109,716 A  *  5/1992  Ito et al. ..................... 73/865.5
5,133,219 A  *  7/1992  Camp ........................ 73/865.5
5,637,810 A  *  6/1997  Conner, Jr. ................ 73/865.5

OTHER PUBLICATIONS

Webster's II New Riverside University Dictionary, 1988, p. 304.*

* cited by examiner

*Primary Examiner*—Daniel S. Larkin
(74) *Attorney, Agent, or Firm*—Robert A. de Groot

(57) ABSTRACT

A method and apparatus for measuring the gas amounts adsorbed on a powder which directly measures pressure changes in a gas supply chamber with the use of differential pressure sensors between the gas supply chamber and a reference chamber which gas amount is maintained constant. Calculations of the gas amounts adsorbed are based on the pressure changes in a sample cell and the pressure changes in the gas supply chamber or a gas reference chamber. The method and apparatus of this invention measures the adsorption or desorption isotherm or gas uptake at constant pressure curve of a powder with, as compared with presently available measurement techniques, increased accuracy and resolution. The experimental data can be analyzed to obtain information on the surface area, pore size distribution, pore volume, pore structure and diffusion coefficient of the powder.

16 Claims, 1 Drawing Sheet

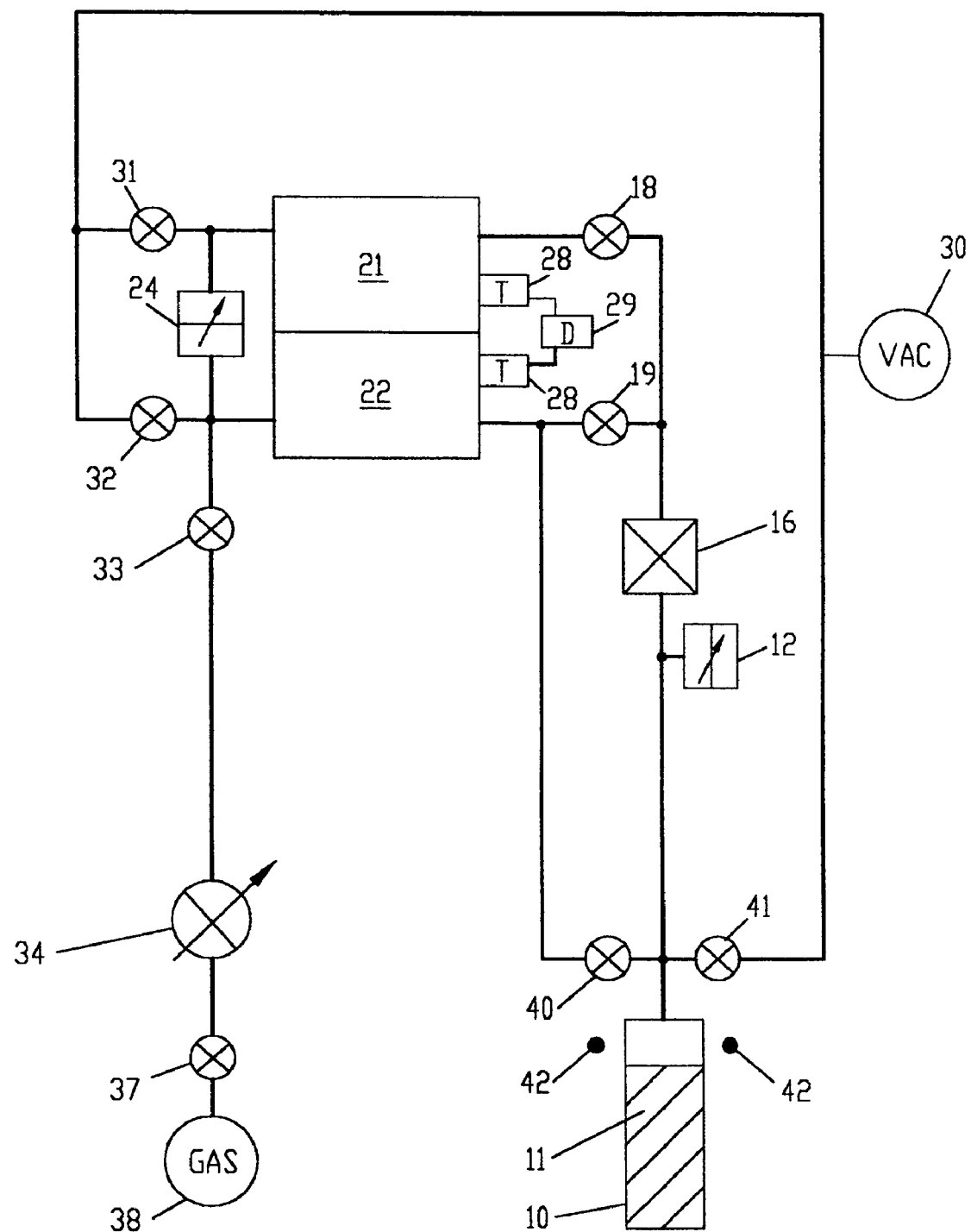

US 6,981,426 B2

METHOD AND APPARATUS TO MEASURE GAS AMOUNTS ADSORBED ON A POWDER SAMPLE

CROSS-REFERENCE TO RELATED APPLICATIONS

Priority is claimed pursuant to 35USC119a,b from People's Republic of China patent application number 03100285.4, filed on Jan. 10, 2003 and continuation-in-part application number 200310113533.2, filed on Nov. 14, 2003.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

Herein, the term "adsorptive" is used to refer to a gas used which is adsorbed, the terms "adsorption isotherm" and "desorption isotherm" refer to data measured and plotted as curves of adsorbed amount versus pressure at a constant temperature onto a powder using physically adsorbed adsorptives, and the term "chemisorption isotherm" refers to similar curves of data measured and plotted but using chemically and selectively adsorbed adsorptives. This invention is related to the practice of measuring adsorption isotherms and desorption isotherms of solid powders, or the practice of measuring chemisorption isotherms of metal particles supported on solid powders, or the practice of measuring gas uptake curves of porous solid powders exposed to a step change in pressure. The measurement of an adsorption-desorption isotherm is also known as the BET (Brunauer, Emmett, Teller) measurement method. The measurement of a chemical adsorption isotherm is also known as the selective gas chemisorption method. The measurement of a gas uptake curve of porous solid powders at constant pressure is also referred to as a diffusivity measurement.

An adsorption isotherm can be analyzed to give the surface area of a powder sample. An adsorption-desorption isotherm can be analyzed to give the pore volume, pore shapes and pore size distribution of powder samples. A chemisorption isotherm can be analyzed to give the surface area and average particle size of catalyst particles on a support. A constant pressure gas uptake curve can be analyzed to give the diffusivity of a gas in a solid. Hereafter, adsorption refers to physical adsorption or chemical adsorption and an adsorption isotherm refers to an adsorption isotherm or a chemisorption isotherm.

The measurement of the gas amounts adsorbed on a solid sample as the pressure surrounding a sample increases gives the adsorption isotherm. Herein, the amount of gas adsorbed on a solid sample includes the gas adsorbed and condensed on the sample. The adsorption measurement is made by dosing amounts of gas into a sample cell, with the amount of gas in each dose known by measurement. The pressure in the sample cell will increase and stabilize at an equilibrium pressure if the rate of gas input is less than the rate of attainment of the equilibrium state. When adsorption occurs onto the sample, the equilibrium pressure is less than it would be without adsorption and the difference in pressure is used to calculate the amount of gas adsorbed on the sample. The amounts of gas adsorbed and the corresponding pressures in the sample cell are the data points of an adsorption or chemisorption isotherm. Successive data points are determined by dosing more gas into the sample cell causing the pressure therein to successively increase. The use of gas laws together with the pressure changes, volume and temperature allows the calculation of the amount of gas added to the free space of the sample cell, and the subtraction of this from the amount of gas dosed gives the adsorbed amount. Herein, free space refers to the space in the sample cell not occupied by sample and includes the volume of connecting conduits and valves. The dosing of gas into the sample cell can be either by a continuous flow method or an intermittent dosing method. A high resolution adsorption isotherm is one where the data points are as closely spaced as possible.

A desorption isotherm is measured similarly to an adsorption isotherm but with the difference that the measurement sequence is carried out in reverse, that is, beginning from where the sample is saturated with gas and then sequentially desorbing adsorbed gas. Herein, the amount of gas desorbed from a solid sample includes the gas desorbed or evaporated from the sample. The measurement commences with the state at the completion of the measurement of an adsorption isotherm, that is, the sample is saturated and the pressure is the saturated vapor pressure at the temperature of the sample (relative pressure of 1.0). The desorption isotherm is measured by measuring the amounts desorbed from the solid sample as the pressure around the sample is successively decreased. The amounts desorbed are measured by flowing gas from the sample cell to a gas chamber kept at a lower pressure, where knowing from measurements the amount of gas that has entered the gas chamber and the amount of gas that has been removed from the free space in the sample cell, the amount of gas desorbed from the sample is calculated from their difference. In this measurement, the rate of gas transfer must be less than the rate of attainment of pressure equilibrium in the sample cell. The amounts that remained adsorbed on the sample, and the corresponding equilibrium pressures in the sample cell are the data points of a desorption isotherm. The gas flow from the sample cell can be either by a continuous flow method or an intermittent dosing method. A high resolution desorption isotherm is one where the data points are as closely spaced as possible.

The basis for the above measurements is to know the total amount of gas supplied to or removed from the sample cell and the amount of gas in the free space of the sample cell. A method used to measure these amounts of gas is based on the use of a chamber of known volume and temperature and a sample cell of known free space and temperature, and the measurements of their pressures at different times to calculate by subtraction the changes in the pressures in the chamber and the sample cell. The gas laws are used to calculate the required amounts of gas. Their difference is the amount of gas adsorbed on the sample.

An embodiment of this method is due to Orr et al. in U.S. Pat. No. 3,850,040. This is an intermittent gas dosing method which used a shut-off valve between a chamber and a sample cell. To measure each adsorption isotherm point, the chamber is filled with gas to a pressure higher than in the sample cell, this pressure measured and then the shut-off valve connecting the sample cell and the chamber is opened until an equilibrium pressure is reached and this pressure is measured. The pressures in the chamber and sample cell before and after the valve is opened are used to calculate their changes in pressure. The amount of gas dosed into the sample cell and the amount of gas accumulated in the free space in the sample cell are then determined using gas laws. Their difference gives the amount of gas adsorbed. Then, the shut-off valve is shut and a repetition of this procedure is used to get the next data point. This is repeated point by point. To measure each desorption isotherm point, the procedure is similar except that the supply chamber is first evacuated to vacuum instead of being first filled with gas and the gas dose is from the sample cell to the chamber. In more modern variants of this method, separate pressure sensors are used to separately measure pressures in the sample cell and chamber. This embodiment has the disadvantage that the chamber has to be refilled or evacuated for each data point measurement.

Another embodiment of this method is shown in U.S. Pat. No. 5,637,810 to Connor. In this, in an adsorption measurement, a dosing manifold is first filled with gas. For each isotherm point, a dosing valve is used to admit a gas dose. The quantity of gas dosed is determined by the pressure in the dosing manifold and the volume of the dosing volume. This is repeated point by point. The dosing volume is made small and a ballast volume is used to provide flexibility in dose sizes. This embodiment has the disadvantage that the dosing manifold has to be refilled a number of times in the course of measuring the isotherms and the dosing volume has to be refilled for each data point measurement.

Additional disadvantages in these apparatuses are that the resolution and accuracy of the isotherm measurements are low. This is because the change in pressure is calculated from two measurements of the pressure. Thus, the dosing volume or chamber has to be of a small size to give measurable changes in its pressure. Due to this small size, the absence of an effective pressure control device in the device and intermittent dosing in discrete units, there are large changes in the pressure in the sample cell with each dose which result in a low resolution of the isotherm, that is, the points of the isotherm are spaced far apart. Also, the supply chamber must be refilled or evacuated many times in measuring an isotherm. This increases the experimental error since as each refill or evacuation gives rise to an experimental error, the errors are proportional to the number of refills. Also, experience is necessary to choose suitable pressures in the dosing volume or chamber and the operation or automation of the measurements requires the manipulation of many valves.

Other embodiments for measuring adsorption-desorption isotherms are shown in U.S. Pat. No. 4,762,010 to Borghard et al. and U.S. Pat. No. 5,109,716 to Ito et al. Borghard et al. used a flow restrictor while Ito et al. used a mass flow controller to control a continuous flow of gas between a supply chamber and a sample cell. The pressures are monitored and calculated changes in the pressures and calculations similar to those described above give the amounts of gas adsorbed or desorbed. As above, the changes in pressure are not themselves directly measured but rather calculated from the two measurements of the pressures at the start and end of some specified time periods. There is a need to ensure pressure quasi-equilibrium in the sample cell, and the flow rate must be kept very slow. One disadvantage in using this method is that the change in pressure in the supply chamber is very small relative to its magnitude, and due to the limited precision of pressure measuring devices, this limits the number of measured points in the isotherm, that is, there is limited resolution. Another disadvantage is again due to the change in pressure in the supply chamber being small relative to its magnitude. Due to the resulting limited precision in calculating the pressure change, this limits the volumetric size of the supply chamber to a small size which has to be small enough to give detectable changes in its pressure with the flow out of it of very small quantities of gas. A small size for the supply chamber has the disadvantage that, as gas is dosed from it, its pressure quickly falls and the supply chamber has to be refilled with gas to a higher pressure many times in the course of measuring an isotherm. The accuracy is limited since the error is proportional to the number of refills because of errors made at each refill. Automation is more complicated because there is also the need to automate the refilling of the supply chamber.

The speed with which a gas can reach the insides of porous solids is necessary information in many uses of powders, and the diffusivity of gases in porous solids is an important characterization of this property. An embodiment for measuring this type of diffusivity is shown in U.S. Pat. No. 4,762,010 to Borghard et al. The method measures the rate of gas uptake upon the application of a constant pressure. This method uses a procedure similar to the measurement of an adsorption isotherm but with the difference that the flow control device between the supply chamber and the sample cell is used to control the gas supply rate to keep the pressure in the sample cell constant. This again requires the control of the gas flow rate at a very slow rate (only the initial surge is fairly large). The disadvantages in the method of Borghard et al. are the same as discussed above, namely, a requirement to keep the flow rate very slow means that the change in pressure in the supply chamber is very small, and due to the limited precision of pressure measuring devices, this limits the number of measured points of the uptake curve, that is, there is limited resolution. Another disadvantage is that the limited precision of the pressure measuring devices limits the volumetric size of the supply chamber to a small size and there is then only a limited pressure range over which uptake curves can be measured.

In a further method to determine an adsorption isotherm, a reference cell is constructed to be virtually the same as a sample cell but used with non-adsorbing blanks in place of a sample, and this is used in conjunction with the sample cell. A supply chamber of known volume and temperature, and a sample cell and needle valve to control adsorptive flow between them constitute a sample subsystem. A second supply chamber with the matching reference sample cell and matching needle valve to control adsorptive flow between them constitute a reference subsystem. The flow rates of adsorptive in the sample subsystem and the reference subsystem are controlled to give matching pressure changes in the sample cell and reference cell, and the pressure difference between the supply chamber and the second supply chamber is measured to determine the amount of adsorptive adsorbed by the sample. A particular embodiment of this method is shown in a paper by Webb (Powder Handling and Processing, Volume 4(4), 1992, 439). The disadvantage of this method is that its construction and operation is quite difficult and expensive because the reference subsystem should precisely match the sample subsystem.

The object of the present invention is to provide an apparatus that does not have the disadvantages discerned above.

SUMMARY OF THE INVENTION

In accordance with a first aspect of this invention, there is provided a method for measuring gas amounts adsorbed by a powder sample in a system comprising a supply chamber of predetermined volume, a reference chamber, a temperature and temperature difference measuring means for said supply chamber and reference chamber, a pressure difference measuring means between said supply chamber and reference chamber, a sample cell of predetermined free space and containing a powder sample, a pressure measuring means for said sample cell, and an evacuating means, the method comprising the steps of:

(a) evacuating said supply chamber, said reference chamber, and said sample cell
(b) providing said powder sample a surrounding of a substantially constant known temperature;
(c) isolating said sample cell, said supply chamber, and said reference chamber from said evacuating means and isolating said sample cell from said supply chamber and said reference chamber;
(d) using a gas supply to supply gas to said supply chamber and said reference chamber, then isolating said supply chamber and said reference chamber from said gas supply by valving means;
(e) isolating said supply chamber from said reference chamber by valving means, waiting for the pressure to stabilize in both chambers, then measuring the pressure difference and temperature difference between them and the temperatures thereof;
(f) supplying gas from said supply chamber to said sample cell using a gas flow control means;
(g) measuring the pressure difference and temperature difference between said reference chamber and said supply chamber and the temperatures thereof, and using said pressure difference, temperature difference, and temperatures, and the volume of said supply chamber, calculating the amount of gas that flowed out from said supply chamber;
(h) measuring the pressure in said sample cell and using said pressure and the free space and temperature of said sample cell, calculating the amount of gas added to the free space in said sample cell;
(i) calculating by the arithmetic difference of the gas amounts in steps (g) and (h) the gas amount adsorbed by said powder sample to get the data point of adsorbed amount at this pressure in said sample cell; and
(j) repeating steps (f) to (i) until the pressure in said sample cell has increased to the required pressure, whereby obtaining data points of adsorbed amount at the increasing pressures in said sample cell.

The method for measuring gas amounts adsorbed by a powder sample further including providing accuracies where the measurement errors are less than 0.3% of their measured readings for the measuring of pressure differences and the measuring of pressures.

The method for measuring gas amounts adsorbed by a powder sample further including providing for said supply chamber and said reference chamber to be at a substantially equal temperature.

The method for measuring gas amounts adsorbed by a powder sample further including providing for the supplying gas to said supply chamber of said step (d) a gas amount such that said supply chamber can supply gas to said sample cell until the pressure therein reaches the pressure required at the end of the adsorption experiment.

The method for measuring gas amounts adsorbed by a powder sample wherein the supplying of gas of said step (f) supplies a continuous flow controlled at a rate such that the pressure in said sample cell is in quasi-equilibrium with the adsorbed gas on said powder sample.

The method for measuring gas amounts adsorbed by a powder sample wherein the supplying of gas of said step (f) supplies an intermittent transfer of gas with waiting for pressure equilibrium to be reached in said sample cell after each transfer of gas before proceeding to step (g).

In accordance with a second aspect of this invention, there is provided an apparatus for measuring gas amounts adsorbed by a powder sample, comprising:

(a) a supply chamber of predetermined volume;
(b) a constant pressure reference chamber connected to said supply chamber by conduits and valving means;
(c) a differential pressure measuring means between said reference chamber and said supply chamber;
(d) temperature sensors contiguous with said reference chamber and said supply chamber, respectively;
(e) a sample cell filled with a powder sample and of predetermined free space;
(f) a gas flow control means with one end connected to said supply chamber and the other end connected to said sample cell;
(g) a pressure measuring means in communication with said sample cell;
(h) a constant temperature surrounding that encloses said powder sample;
(i) evacuating means connected to said supply chamber, said reference chamber, and said sample cell by connecting conduits and valving means; and
(j) a gas supply connected to said supply chamber and said reference chamber by connecting conduits and valving means.

The apparatus for measuring gas amounts adsorbed by a powder sample wherein said differential pressure measuring means and said pressure measuring means are pressure sensors with measurement errors less than 0.3% of the measured readings.

The apparatus for measuring gas amounts adsorbed by a powder sample wherein said gas flow control means is a leak valve.

The apparatus for measuring gas amounts adsorbed by a powder sample wherein said gas flow control means is a shut-off valve.

The apparatus for measuring gas amounts adsorbed by a powder sample wherein said gas flow control means is a mass flow control device.

The apparatus for measuring gas amounts adsorbed by a powder sample wherein said supply chamber and said reference chamber are containers that are thermally contiguous.

The apparatus for measuring gas amounts adsorbed by a powder sample wherein said supply chamber is a container with the gas amount to increase the pressure in said sample cell to the pressure required at the end of the adsorption experiment.

The apparatus for measuring gas amounts adsorbed by a powder sample further including a differential temperature measuring means contiguous with said supply chamber and said reference chamber, respectively.

In accordance with the first aspect of this invention, there is provided a method for measuring gas amounts adsorbed by a powder sample in a system comprising a supply chamber of predetermined volume, a reference chamber, a temperature measuring means for said supply chamber and reference chamber, a pressure difference measuring means between said supply chamber and reference chamber, a sample cell of predetermined free space and containing a powder sample, a pressure measuring means for said sample cell, and an evacuating means, the method comprising the steps of:

(a) evacuating said supply chamber, said reference chamber, and said sample cell;

(b) providing said powder sample a surrounding of a substantially constant known temperature;
(c) isolating said sample cell, said supply chamber, and said reference chamber from said evacuating means and isolating said sample cell from said supply chamber and said reference chamber;
(d) using a gas supply to supply gas to said supply chamber and said reference chamber, then isolating said supply chamber and said reference chamber from said gas supply by valving means;
(e) isolating said supply chamber from said reference chamber by valving means, waiting for the pressure to stabilize in both chambers, then measuring the pressure difference between them and the temperatures thereof;
(f) supplying gas from said supply chamber to said sample cell using a gas flow control means;
(g) measuring the pressure difference between said reference chamber and said supply chamber and the temperatures thereof, and using said pressure difference and temperatures, and the volume of said supply chamber, calculating the amount of gas that flowed out from said supply chamber;
(h) measuring the pressure in said sample cell and using said pressure and the free space and temperature of said sample cell, calculating the amount of gas added to the free space in said sample cell;
(i) calculating by the arithmetic difference of the gas amounts in steps (g) and (h) the gas amount adsorbed by said powder sample to get the data point of adsorbed amount at this pressure in said sample cell;
(j) repeating steps (f) to (i) until the pressure in said sample cell has increased to the required pressure, whereby obtaining data points of adsorbed amount at the increasing pressures in said sample cell;
(k) providing for said reference chamber a predetermined volume;
(l) following step (j), isolating said sample cell from said supply chamber and said reference chamber, and evacuating to vacuum said supply chamber and said reference chamber;
(m) isolating said reference chamber from said supply chamber and said evacuating means, and continue evacuating said supply chamber;
(n) supplying gas from said sample cell to said reference chamber using said gas flow control means;
(o) measuring the pressure and temperature of said reference chamber, and using the pressure, temperature, and volume of said reference chamber, calculating the amount of gas added to said reference chamber;
(p) measuring the pressure in said sample cell, calculating the change in pressure in said sample cell, and using this pressure change, free space, and temperature of said sample cell, calculating the amount of gas removed from the free space in said sample cell;
(q) calculating the arithmetic difference of the gas amounts of steps (o) and (p) to calculate the gas amount desorbed by said powder sample, and subtracting this desorbed amount from the amount adsorbed at the highest pressure in step (j) to get a data point of adsorbed amount at this pressure in said sample cell; and
(r) repeating steps (n) to (q) until the pressure in said sample cell has fallen to a specified pressure, whereby obtaining said data points of adsorbed amount at the decreasing pressures in said sample cell.

The objects and advantages of the invention are the measurements of gas amounts adsorbed by a powder sample with higher precision, resolution and accuracy than prior art and it differs from prior art in the use of a differential pressure measuring means and a reference chamber which gas amount is kept constant to measure the pressure change in a supply chamber, and the provision for the supply chamber to have a gas amount to supply gas to the sample cell until its pressure attains the pressure required at the end of the adsorption experiment without a need to refill the supply chamber.

A highly advantageous effect in the invention is in the direct measurement of pressure differences. These measurements are performed with highly accurate differential pressure sensors with very small experimental errors. The direct measurement of pressure differences is highly significant because very small pressure differentials can be measured with high accuracy with highly accurate differential pressure sensors. Prior arts do not measure directly such pressure differences but instead derive them indirectly by calculating them by arithmetic subtraction from the measurements of the pressures at two different times. Due to that the magnitudes of the pressures can be each much larger than their difference, and there are errors in their measurements, the resulting much smaller number from their subtraction will have a large uncertainty.

The invention gives experimental results with higher resolution in addition to higher precision because unlike prior art that used calculated pressure changes, the direct measurement of pressure differences allows data to be taken at very small intervals of pressure differences, whereas prior art measurements can only be taken at intervals of pressure differences that are large enough to be significant with respect to the precision with which pressures can be measured.

The invention gives experimental results with higher accuracy due to the use of a supply chamber with a gas amount to supply gas such that the pressure in the sample cell can reach the pressure required at the end of the adsorption experiment without a need to refill the supply chamber. This is different from the prior art where the supply chamber is small and it experiences significant pressure drop after supplying some gas, which leads to a need for the supply chamber to be refilled with gas many times during a measurement, resulting in its accuracy being poorer due to the cumulative error from the addition of the errors made at each refill.

Due to that there is no need for multiple refilling of the supply chamber, it is easy to automate the measurements.

BRIEF DESCRIPTION OF THE DRAWING

The FIGURE is a schematic view of an apparatus used for measuring the gas amounts adsorbed by a powder sample.

REFERENCE NUMERALS IN THE DRAWING

10—sample cell; 11—sample; 12—pressure measuring means; 16—gas flow control means; 18—shut-off valve; 19—shut-off valve; 21—supply chamber; 22—reference chamber; 24—differential pressure measuring means; 28—temperature sensor; 29—temperature measuring device; 30—evacuating means; 31—shut-off valve; 32—shut-off valve; 33—shut-off valve; 34—needle valve; 37—shut-off valve; 38—gas supply; 40—shut-off valve; 41—shut-off valve; 42—constant temperature surrounding;

DETAILED DESCRIPTION OF THE INVENTION—PREFERRED EMBODIMENT

The FIGURE shows a preferred embodiment of the apparatus of the present invention. The gas used depends on the nature of adsorption desired which can be either physical or chemical, and if chemical on whether adsorption is carried out under conditions of equilibrium or of constant pressure. These are usually known as measuring an adsorption isotherm, a chemisorption isotherm or a constant pressure gas uptake curve, respectively. Gases traditionally used for physical adsorption include nitrogen, argon, kiypton, hydrocarbons (e.g. butane and hexane), water and carbon dioxide. Gases traditionally used for chemical adsorption include hydrogen, carbon monoxide, oxygen, and the like.

The apparatus measures the amounts of gas adsorbed on a powder sample 11. Powder sample 11 is placed in a sample cell 10, and the part of sample cell 10 which contains sample 11 is completely immersed in a constant temperature surrounding 42. Constant temperature surrounding 42 is a liquid nitrogen bath for measurements using nitrogen. For experiments at another temperature, it would be a bath or temperature-controlled oven at that temperature. The experiment measures the pressure in sample cell 10. This pressure is measured by a pressure measuring means 12 and recorded by a computer device (not shown in the FIGURE). Pressure measuring means 12 comprises highly accurate pressure sensors, e.g. MKS Baratron Type 120 or Type 690A capacitance-based diaphragm pressure sensors, of different full ranges of 0.1 torr, 10 torr and 1000 torr. These instruments have experimental errors that are very small fixed percentages, generally less than 0.3%, of the measured reading. Such sensors are available from MKS Instruments Co. of Burlington, Mass. In other apparatuses, the pressure measuring means can be other pressure sensors, e.g. one or more pressure heads of different ranges according to the range desired of the isotherm or it can be differential pressure sensors referenced to a vacuum.

Sample cell 10 can be evacuated by an evacuating means 30 through a valve 41. Valve 41, and valves 18, 19, 31, 32, 33, 37, 40, and 41 are shut-off valves, but other types of valves e.g. solenoid valves, that can be used as open-shut valving control can be used. Evacuating means 30 is a turbomolecular pump and mechanical pump combination but can also be other similar vacuum pumps. Sample cell 10 is connected to a gas flow control means 16 by conduits. The volume of the space within the sample cell that is not occupied by sample 11 is known as the free space. When the free space of sample cell 10 is referred to, it is to be understood that this free space volume includes the volume of all relevant conduits, e.g. for the apparatus in the FIGURE, this includes the conduits leading to gas flow control means 16, valve 40, valve 41 and pressure measuring means 12. In many experiments, sample 11 is kept at a temperature different from the ambience temperature of most of the other elements and conduits. Hereafter, when the free space of sample cell 10 is referred to, it is to be understood that this includes a correction for the difference in temperatures and if at the temperature of sample 11, the gas behaves as a non-ideal gas, the portion of free space in sample cell 10 that is at this temperature is also correspondingly corrected to take into account non-ideal behavior.

Gas flow control means 16 is a fine control needle leak valve capable of controlling gas flow through it to very slow rates. It is a type of variable leak throttling valve commonly used for dosing gases into ultra-high vacuum chambers. Such leak valves are available from, e.g., Varian, Inc. Gas flow control means 16 is used to control the gas flow to or from sample cell 10 at a rate slow enough to ensure pressure quasi-equilibrium in the sample cell. Quasi-equilibrium means that the pressure in the sample cell will not change if the gas flow is stopped. The flow rate through gas flow control means 16 may be changed during the course of an experiment, that is, the gas flow control means is not used to control a constant flow rate, but the flow rate is used that is convenient and which is sufficiently slow enough to maintain pressure quasi-equilibrium in sample cell 10 in measuring isotherms or to maintain a constant pressure in sample cell 10 in measuring uptake curves. Changes to the flow rate through gas flow control means 16 may be performed manually or by computer control by a stepper motor (not shown in the FIGURE). There is no need for the flow rate to be measured nor known. In other apparatuses, gas flow control means 16 can be a mass flow controller or a shut-off valve.

The other side of gas flow control means 16 is connected to a supply chamber 21 by conduits. Supply chamber 21 is used to supply gas to sample cell 10. The volume of supply chamber 21 is predetermined by prior measurements, and is to be understood to include the volumes of the relevant conduits, e.g. for the apparatus in the FIGURE, this includes the conduits between supply chamber 21 and valve 18, valve 19 and valve 31, gas flow control means 16 and a differential pressure measuring means 24. The experiment measures the pressure changes in supply chamber 21. These pressure changes are measured by differential pressure measuring means 24 which is connected to supply chamber 21. Differential pressure measuring means 24 is used to measure pressure changes in the supply chamber by connecting the other side of said pressure differential pressure measuring means to a reference chamber 22 which gas amount is kept constant, that is, when the gas amount in reference chamber 22 is constant, the pressure difference between reference chamber 22 and supply chamber 21 is the pressure change in supply chamber 21. Since the pressure is affected by changes in the temperature, the invention further includes for reference chamber 22 to be in thermal contact with supply chamber 21 to minimize temperature effects, and the precision with which their temperature difference is measured is increased by further using a pair of thermocouples in contact with supply chamber 21 and reference chamber 22, respectively. In other apparatuses, reference chamber 22 and supply chamber 21 can be placed in a constant temperature bath to minimize temperature effects. Differential pressure measuring means 24 comprises highly accurate differential pressure sensors, e.g. MKS Baratron Type 120, Type 698A or Type 223B capacitance-based diaphragm differential pressure sensors, of different full ranges of 10 torr and 1000 torr. These instruments have experimental errors that are very small fixed percentages, generally less than 0.3%, of the measured reading. The differential pressure sensors are connected with the lower pressure side as the pressure in supply chamber 21 and the higher pressure side as the pressure in reference chamber 22 and they can measure accurately even very small pressure differences. They are remotely monitored by a computer device (not shown in the FIGURE). Such sensors are available from MKS Instruments Co. of Burlington, Mass. These are examples and one can also use other differential pressure transducers, e.g. one or more heads with different pressure ranges. In other apparatuses, the pressure heads can be other pressure ranges according to the requirements of the isotherm.

The significant advantage of using differential pressure transducers is that very small changes in the pressure in supply chamber 21 can be accurately and precisely measured by keeping the gas amount in reference chamber 22 constant. Very small changes cannot be detected in the techniques of the prior art. The prior art measures the pressure change indirectly by measuring the absolute pressures of a supply chamber at different times and then calculates pressure changes as arithmetic differences, which is much less accurate as it involves the subtraction of a large number from another large number to calculate a small difference.

Supply chamber 21 and reference chamber 22 can be evacuated by evacuating means 30 through valve 31 and valve 32, respectively, and can be supplied with gas by a gas supply 38 and valve 37, and needle valve 34 and valve 33, and valve 19 and valve 18. More gas supplies can be included if needed. Supply chamber 21 can be separated from reference chamber 22 by valve 18 and valve 19. Since the pressure is affected by changes in the temperature, the temperatures of supply chamber 21 and reference chamber 22 are measured using temperature sensors 28 that are contiguous with each chamber, respectively and a temperature measuring device 29. In an adsorption measurement, it is actually the temperature of supply chamber 21 and the temperature difference between supply chamber 21 and reference chamber 22 that are needed. In principle, the temperature difference can be obtained from the temperatures of supply chamber 21 and reference chamber 22 by subtraction, but the invention further includes a direct measurement of the temperature difference to give increased precision. The temperature sensors contiguous with supply chamber 21 and reference chamber 22 are thermocouples, two for each chamber, with one thermocouple of each chamber respectively referenced to an electronic cold junction compensation in temperature measuring device 29 to measure the temperature of the respective chamber, and the second thermocouples of each chamber respectively are connected together to measure the temperature difference between the chambers. Temperature measuring device 29 is a special design multi-channel voltage amplifier that amplifies thermocouple signals and which directly measures the temperature difference signal between supply chamber 21 and reference chamber 22, and it includes electronic cold junction compensation when used to measure the temperatures of supply chamber 21 and reference chamber 22. The temperature of the other parts of the apparatus, except the part enclosed in the constant temperature surrounding, is assumed to be at ambient temperature. The ambient temperature is measured by an alcohol glass thermometer (not shown). In other apparatuses, other temperature sensors and temperature measuring devices can also be used.

Operation of the apparatus shown in the FIGURE is now described. A precisely weighed amount of about 0.2 g of sample 11 is placed in sample cell 10. The pretreatment of sample 11 and the measurement of the free space of sample cell 10 are first performed before measuring the gas amounts adsorbed by the sample 11. For some types of sample, sample pretreatment may require a flowing gas and a specially designed sample cell (special design not shown here) is used. The details of sample pretreatment depend on the sample and are not described here. The measurement of the free space of sample cell 10 is described below in conjunction with the example. After the free space in sample cell 10 has been determined, gas flow control means 16 is shut and sample 11 and sample cell 10 are evacuated through valve 41. Supply chamber 21 and reference chamber 22 are evacuated, then isolated from vacuum by valve 31 and valve 32 and, with valve 40 kept closed, filled with gas from gas supply 38 and valve 37 through needle valve 34, valve 33, valve 19 and valve 18. The gas pressure is chosen by previous experiments and experience of the operator to ensure that there is sufficient gas to complete the experiment without the need to refill supply chamber 21. For 0.2 g of a sample with a surface area about 300 $m^2/g$, and supply chamber 21 of 200 cc, a pressure of 900 torr is usually used. The gas supply is then isolated by shutting valve 33 and valve 37. Reference chamber 22 is isolated from supply chamber 21 by shutting valve 19 and their pressure difference, temperatures and temperature difference are measured. Sample cell 10 is isolated from vacuum by shutting valve 41.

Before making the measurements, sample 11 is put at a required temperature by surrounding it with constant temperature surrounding 42. The temperature is usually liquid nitrogen temperature for an adsorption or desorption isotherm and room temperature for a chemisorption isotherm. Then, gas flow control means 16 is opened and used to control the gas flow from supply chamber 21 to sample cell 10 to begin the measurement. The rate of gas flow is chosen by previous experiments and experience of the operator to be slow enough to ensure that pressure quasi-equilibrium in sample cell 10 is attained, that is, if gas flow control means 16 is shut, there will not be any change in the pressure in sample cell 10. The flow rate is typically such that the pressure rise in sample cell 10 is about 15–70 torr per hr but other values may also be used. With most systems, a simple check on whether quasi-equilibrium is attained is to compare the recorded adsorption isotherm for two different flow rates of the gas, e.g. in a ratio of 1 to 2, and if the isotherms are identical, they can be assumed to be equilibrium isotherms. The pressure difference between reference chamber 22 and supply chamber 21, the pressure in sample cell 10, the ambient temperature, the temperature of supply chamber 21 and the temperature difference between supply chamber 21 and reference chamber 22 are measured and recorded continuously by a data acquisition computer (not shown). For an adsorption isotherm, the measurements are continued until the pressure in sample cell 10 reaches the saturated vapor pressure of the gas at the temperature of the sample or to about atmospheric pressure. For a chemisorption isotherm, the experiment is continued until the sample is saturated with gas, which is about 50 torr. For an uptake curve at constant pressure, the experiment is continued until the sample is saturated with gas.

In the above operation, a continuous flow of gas is used to dose sample 11. An alternative mode is to use an intermittent transfer of gas to dose the sample. In this mode, gas flow control means 16 is opened for only a short time and then is closed until pressure equilibrium is reached in supply chamber 21 and sample cell 10, then the relevant pressure, pressure difference, temperatures and temperature difference readings are taken and recorded. The open-shut operation of gas flow control means 16 is repeated to measure the isotherm point by point.

It will be seen from the above description that there is no need to refill supply chamber 21 in the course of the experiment, and as such it differs from prior art, e.g. the method in the Borghard et al. disclosure described above. As discussed above, this is an important object of the invention, that is, avoiding the need to refill supply chamber gives increased accuracy and simplifies the automation of the apparatus.

The above described the measuring of an adsorption isotherm, a chemisorption isotherm or a constant pressure gas uptake curve. The basic elements of the apparatus and operation for measuring a desorption isotherm are now described. Valve 40 and its connecting conduit is used to provide sample cell 10 with a high conductance pathway in the very low pressure region during desorption. During the measurement of a desorption isotherm, supply chamber 21 is evacuated to vacuum then isolated by closing valve 18 and used as a vacuum reference for differential pressure measuring means 24. With this reference, differential pressure measuring means 24 measures the pressure in reference chamber 22. The volume of reference chamber 22 is predetermined by prior measurements, and is to be understood to include the volumes of the relevant conduits, e.g. for the apparatus in the FIGURE, this includes the conduits between reference chamber 22 and valve 18, valve 32, valve 33 and valve 40, gas flow control means 16 and differential pressure measuring means 24.

The measurement of a desorption isotherm begins with sample cell 10 and sample 11 in the state at the end of an adsorption experiment, that is, the pressure in sample cell 10 is the saturated vapor pressure of the gas at the sample temperature or about atmospheric pressure and gas has adsorbed to equilibrium on sample 11 at this pressure. Gas flow control means 16 is shut and supply chamber 21 and reference chamber 22 are evacuated to vacuum by opening valve 31 and valve 32. Valve 32 is then closed, and supply chamber 21 isolated from reference chamber 22 by shutting valve 18, and supply chamber 21 is kept evacuated.

With valve 18 maintained shut, gas flow control means 16 is opened and used to control the gas flow from sample cell 10 to reference chamber 22 at a rate slow enough to ensure that pressure quasi-equilibrium in sample cell 10 is maintained with respect to desorption, that is, if gas flow control means 16 is shut off, there will not be any substantial change in the pressure in sample cell 10. The pressure difference in reference chamber 22 with respect to supply chamber 21 (which is the pressure in reference chamber 22), the pressure in sample cell 10, ambient temperature and the temperature of supply chamber 21 and the temperature difference between supply chamber 21 and reference chamber 22 are measured and recorded continuously by a data acquisition computer (not shown). The measurements are continued until the pressure in sample cell 10 and the pressure in reference chamber 22 are almost equal and there is almost no gas flow through gas flow control means 16. Then gas flow control means 16 is shut off. For a reference chamber 22 with a volume of 500 c.c. and a sample with a surface area of about 60 m$^2$, the pressure of reference chamber 22 at the end of this experiment is about 100 torr. If it is necessary to carry on the experiment to lower pressures, with gas flow control means 16 closed, reference chamber 22 is evacuated to vacuum. Then gas flow control means 16 is opened and the measurement operation above is repeated. The number of times reference chamber 22 is evacuated is kept to a minimum by choosing an appropriate volume for the reference chamber.

In the above operation, a continuous flow of gas is used to transfer gas from sample cell 10 to reference chamber 22. An alternative mode is to use the intermittent gas dosing method. In this mode, gas flow control means 16 is opened for only a short time and then is closed until pressure equilibrium is reached in sample cell 10 and reference chamber 22, then the relevant pressure, pressure difference, ambient temperature and temperature and temperature difference readings are recorded. The open-shut operation of gas flow control means 16 is repeated to measure the isotherm point by point.

For some samples or some high boiling point gas, the very low pressure region of the desorption isotherm is of much significance. At very low pressures, there can be almost no gas flow through gas flow control means 16 and it is shut off. Valve 40 is then used to control the measurement of the desorption isotherm using a point-by-point method. Each point is measured as follows. With valve 40 shut, reference chamber 22 is evacuated to vacuum through valve 32. Then valve 32 is shut and valve 40 is open to transfer gas from sample cell 10, meanwhile noting the pressure drop in sample cell 10 and shutting off valve 40 at the appropriate pressure. This should be a pressure, based on operator experience, that gives a reasonably spaced point on the desorption isotherm. When equilibrium is reached in sample cell 10 and in reference chamber 22, their pressures, the relevant temperatures and temperature difference readings are recorded. This will give a point on the desorption isotherm. The conduit is again evacuated to vacuum and the procedure is repeated to a lower pressure in sample cell 10.

The novel aspect of this invention of measuring differential pressures allows the changes in the gas content in supply chamber 21 to be very precisely determined and this obviates the need for the flow rate to be controlled very constant or otherwise needing a method for its calculation. Another novel aspect is that supply chamber 21 is initially provided with sufficient gas to supply sample cell 10 and sample 11 to reach the highest pressure therein required by the experiment without a refill of supply chamber 21. This gives increased accuracy over the prior art. The prior art uses the subtraction of the pressures measured at two different times to get the pressure change, thus, it needs a supply chamber with a small volume so that the flow out from it of a small amount of gas can give a measurable pressure change. But then the pressure drop is faster and the pressure in the supply chamber soon falls to be near the pressure in sample cell 10 and this causes the need for many gas refills in the course of the experiment to increase the pressure in the supply chamber. Due to that there is an uncertainty associated with the pressure reading of each refill, the overall experimental precision is adversely affected by the number of refills.

EXAMPLE

An example of a nitrogen adsorption and desorption experiment follows. The free space in sample cell 10 which is the volume of sample cell 10 not occupied by sample 11, is first determined. Then, the adsorption isotherm and the desorption isotherm are measured. In the following, the volume of supply chamber 21 includes the volume of conduits to gas flow control means 16, and the volume of free space in sample cell 10 includes the volume of conduits to gas flow control means 16. The volume of supply chamber 21 is already precisely predetermined from previous measurements.

1. Measurement and Calculation of the Free Space in Sample Cell 10.

The free space in sample cell 10 is determined by gas law relationships using a three step procedure. In the first step, the free space at ambient temperature of sample cell 10 without any sample is measured. Empty sample cell 10 is isolated from supply chamber 21 and reference chamber 22 and sample cell 10 is evacuated. Supply chamber 21 and reference chamber 22, after evacuation, are connected and filled with nitrogen. Then, sample cell 10 is isolated from vacuum by valve 41, sample cell 10 is kept at ambient temperature, supply chamber 21 is isolated from reference chamber 22, and sample cell 10 and supply chamber 21 are connected. After some nitrogen had been dosed into sample cell 10, sample cell 10 and supply chamber 21 are isolated. The pressure differential between reference chamber 22 and supply chamber 21, pressure in sample cell 10, ambient temperature and the temperature of supply chamber 21 and the temperature difference between supply chamber 21 reference chamber 22 are measured.

In the second step, empty sample cell 10 with the part of it that will contain sample 11 is immersed in constant temperature surrounding 42, which is a liquid nitrogen bath in this example, taking care to ensure that the length of sample cell 10 that is in contact with liquid nitrogen can be accurately reproduced. The pressure in sample cell 10 is measured. During this measurement, part of sample cell 10 is immersed in a liquid nitrogen bath and part is kept at ambient temperature, and there is a transitional part between these two parts where the temperature varies from liquid nitrogen temperature to ambient temperature. In the calculation, this is simplified as if there is a sharp change from liquid nitrogen temperature to ambient temperature, that is, the total free space of sample cell 10 is divided into a volume of free space at liquid nitrogen temperature and a volume of free space at ambient temperature.

In the third step, a precisely weighed amount of about 0.2 g of sample 11 is put into sample cell 10. After suitable sample pre-treatment, the free space taken up by sample 11 is determined by measuring the free space at ambient temperature of sample cell 10 filled with sample 11 and by subtracting this from the free space at ambient temperature of sample cell 10 without any sample. This step is similar to the first step above except that sample cell 10 is now filled with sample 11; if the sample adsorbs nitrogen, helium should be used in this step.

Let V1 denote the volume of supply chamber 21, V1=201.7 cc (prior measurement), T1 denote the temperature of supply chamber 21, V2 denote the volume of free space in empty sample cell 10 at ambient temperature, T2 denote the temperature of the part of sample cell 10 not immersed in liquid nitrogen (taken to be the ambient temperature), Vu denote the volume of free space in sample cell 10 that is at ambient temperature when sample cell 10 is immersed in liquid nitrogen, Vc denote the volume of free space in sample cell 10 that is at liquid nitrogen temperature when sample cell 10 is immersed in liquid nitrogen, T3 denote the temperature of that part of sample cell 10 in contact with liquid nitrogen, (taken to be liquid nitrogen temperature), dP1 denote the pressure differential between reference chamber 22 and supply chamber 21 after nitrogen had been dosed into sample cell 10 in step 1; from the measurement of the temperature difference between supply chamber 21 and reference chamber 22, if the temperature difference had changed, Charles Law is used to calculate the effect of temperature on the pressure in reference chamber 22 to nullify the effect of temperature on dP1.

P1 denote the pressure in empty sample cell 10 after nitrogen had been dosed into it and it is kept at ambient temperature in step 1, P2 denote the pressure in empty sample cell 10 after sample cell 10 is immersed in liquid nitrogen in step 2, V3 denote the volume of free space in sample cell 10 filled with sample 11 and at ambient temperature, dP3 denote the pressure differential between reference chamber 22 and supply chamber 21 after nitrogen had been dosed into sample cell 10 in step 3; from the measurement of the temperature difference between supply chamber 21 and reference chamber 22, if the temperature difference had changed, Charles Law is used to calculate the effect of temperature on the pressure in reference chamber 22 to nullify the effect of temperature on dP3.

P3 denote the pressure in sample cell 10 filled with sample 11 after nitrogen had been dosed into it and it is kept at ambient temperature in step 3, Vd denote the volume of free space in sample cell 10 that is at liquid nitrogen temperature when sample cell 10 containing sample 11 is immersed in liquid nitrogen, which differs from Vc in that Vc is empty and Vd is filled with sample 11.

Let N1 denote the amount of nitrogen that flowed out from supply chamber 21 in step 1:

$$N1 = \frac{dP1 \times V1}{R \times T1} \quad \text{equation (1)}$$

N1 is the amount of nitrogen that flowed into sample cell 10, thus:

$$N1 = \frac{P1 \times V2}{R \times T2} \quad \text{equation (2)}$$

from which V2 is obtained.

N1 is also the amount of nitrogen in sample cell 10 when it is immersed in the liquid nitrogen bath, thus:

$$N1 = \frac{P2 \times Vu}{R \times T2} + \frac{P2 \times Vc}{R \times T3}(1 + \alpha P2) \quad \text{equation (3)}$$

where non-ideal behavior at liquid nitrogen temperature is accounted for by using $$N = \frac{P \times V}{R \times T}(1 + \alpha P)$$

where $\alpha$ is a non-ideality correction factor; $\alpha = 5.333 \times 10^{-5}$ torr$^{-1}$ for nitrogen at 77.4 K when P is expressed in torrs.

Since Vu=V2−Vc  equation (4)

$$N1 = \frac{P2 \times (V2 - Vc)}{R \times T2} + \frac{P2 \times Vc}{R \times T3}(1 + \alpha P2) \quad \text{equation (5)}$$

from which Vc is obtained, and Vu is also obtained.

Let N3 denote the amount of nitrogen that flowed out from supply chamber 21 in step 3:

$$N3 = \frac{dP3 \times V1}{R \times T1} \quad \text{equation (6)}$$

N3 is the amount of nitrogen added to sample cell 10, thus:

$$N3 = \frac{P3 \times V3}{R \times T2} \quad \text{equation (7)}$$

from which V3 is obtained, and the space occupied by the sample is calculated and hence, Vd is obtained by subtraction from Vc.

A detailed example calculation follows.

Step 1:

Measured data: V1=201.7 cc, T1=293.0 K, dP1=9.45 torr, P1=125.3 torr, T2=293.0 K.

R=0.062364 torr cc/($\mu$mol K).

From equation (1), N1=9.45×201.7/(0.062364×293.0)=104.31 $\mu$mol.

From equation (2), V2=104.31×0.062364×293.0/125.3=15.21 cc.

Step 2:

Measured data: P2=70.5 torr, T2=293 K, T3=77.4 K.

From equation (5):

104.31=70.5×(15.21−Vc)/(0.062364×293.0)+70.5×Vc/(0.062364×293.0)×(1.0+5.333×10$^{-5}$×70.5), whence Vc=4.22 cc.

and from equation (4), Vu=15.21−4.22=10.99 cc.

Step 3:

Measured data: V1=201.7 cc, T1=293.0 K, dP3=8.55 torr, P3=119.68 torr, T2=293.0 K.

From equation (6), N3=8.55×201.7/(0.062364×293.0)=94.38 $\mu$mol.

From equation (7), V2=94.38×0.062364×293.0/119.68=14.41 cc.

Vd=Vc−(V2−V3)=4.22−(15.21−14.41)=3.41 cc.

2. Adsorption

After measuring the free space in sample cell 10, sample cell 10 is isolated from supply chamber 21 and reference chamber 22, and evacuated. Meanwhile, supply chamber 21 and reference chamber 22 are connected to bring them to equal pressure and if needed, nitrogen is added to bring the pressure to about 900 torr. Then, sample cell 10 is isolated from vacuum by valve 41 and the part containing sample 11 is maintained at liquid nitrogen temperature, supply chamber 21 is isolated from reference chamber 22, and sample cell 10 and supply chamber 21 are connected through gas flow control means 16 and nitrogen is slowly continuously leaked into sample cell 10. The pressure differential between reference chamber 22 and supply chamber 21, pressure in sample cell 10, ambient temperature and the temperature of supply chamber 21 and temperature difference between supply chamber 21 reference chamber 22 are measured.

Let V1 denote the volume of supply chamber 21, V1=201.7 cc (prior measurement), T1 denote the temperature of supply chamber 21, T2 denote the temperature of the part of sample cell 10 not immersed in liquid nitrogen, (taken to be the ambient temperature), Vu denote the volume of free space in sample cell 10 that is at ambient temperature when sample 11 is immersed in liquid nitrogen; Vu=10.99 cc as measured above;

Vd denote the volume of free space in sample cell 10 and sample ii that is at liquid nitrogen temperature, Vd=3.41 cc as measured above;

T3 denote the temperature of the part of sample cell 10 in contact with liquid nitrogen, (taken to be liquid nitrogen temperature), dP denote the pressure difference between reference chamber 22 and supply chamber 21 at time t; from the measurement of the temperature difference between supply chamber 21 and reference chamber 22, if the temperature difference had changed, Charles Law is used to calculate the effect of temperature on the pressure in reference chamber 22 to nullify the effect of temperature on dP.

P denote the pressure in sample cell 10 at time t.

Let N4 denote the amount of nitrogen removed from supply chamber 20:

$$N4 = \frac{dP \times V1}{R \times T1} \quad \text{equation (8)}$$

N4 has a part added to the free space of sample cell 10 and a part adsorbed on sample 11. Let N5 denote the amount of nitrogen in the free space of sample cell 10. Using the ideal gas law for the gas at ambient temperature and a correction for non-ideality for the gas at liquid nitrogen temperature:

$$N5 = \frac{P \times Vu}{R \times T2} + \frac{P \times Vd}{R \times T3}(1 + \alpha P). \quad \text{equation (9)}$$

where $\alpha$ is as in equation (3). Supposed it is measured that T1=298.0 K, T2=298.0 K, T3=77.4 K. Let Na be the amount of gas adsorbed. Na can be obtained by N4−N5. The columns of Table 1 indicate data that may be obtained, and calculated N4, N5 and Na.

TABLE 1

Adsorption Data

| Time/s | dP/torr | P/torr | N4/$\mu$mol | N5/$\mu$mol | Na/$\mu$mol |
|---|---|---|---|---|---|
| 0 | 0.0000 | 0.0000 | 0.0 | 0.0 | 0.0 |
| 5.0 | 0.290 | 0.110 | 3.147 | 0.143 | 3.004 |
| 10.0 | 0.357 | 0.200 | 3.875 | 0.260 | 3.615 |

A plot of Na versus P is the adsorption isotherm. In Table 1, dP is data measured using differential pressure sensors between reference chamber 22 and supply chamber 21. The fine resolution of these data cannot be obtained from the subtraction of two measured pressures.

3. Desorption

After measuring the points of the adsorption isotherm to a relative pressure of 1.0, sample cell 10 is isolated from supply chamber 21. Reference chamber 22, supply chamber 21 and reference chamber 22 are evacuated to vacuum. Supply chamber 21 is isolated from reference chamber 22, and supply chamber 21 is kept evacuated. With sample cell 10 maintained immersed in liquid nitrogen, reference chamber 22 and sample cell 10 are connected through gas flow control means 16 and nitrogen is slowly continuously leaked out from sample cell 10. The pressure differential between supply chamber 21 and reference chamber 22, pressure in sample cell 10, ambient temperature, temperature of supply chamber 21 and temperature difference between supply chamber 21 and reference chamber 22 are measured.

Let V4 denote the volume of reference chamber 22, V4=978.6 cc (prior measurement), T4 denote the temperature of reference chamber 22, T2 denote the temperature of sample cell 10 not immersed in liquid nitrogen (taken to be the ambient temperature), Vu denote the volume of free space in sample cell 10 that is at ambient temperature when sample 11 is immersed in liquid nitrogen, Vu=10.99 cc as measured above;

Vd denote the volume of free space in sample cell 10 and sample 11 that is at liquid nitrogen temperature, Vd=3.41 cc as measured above;

T3 denote the temperature of the part of sample cell 10 in contact with liquid nitrogen, (taken to be liquid nitrogen temperature), dP denote the pressure differential between reference chamber 22 and supply chamber 21 at time t, P denote the pressure in sample cell 10 at time t, P0 denote the saturated vapor pressure of nitrogen at liquid nitrogen temperature; this is P at start of the desorption measurement.

Let N6 denote the amount of nitrogen added to reference chamber 22:

$$N6 = \frac{dP \times V4}{R \times T4} \qquad \text{equation (10)}$$

N6 is the amount of nitrogen transferred from sample cell 10 and sample 11, and has contributions separable into a part from the free space of sample cell 10 and a part desorbed from sample 11. Let N5 denote the amount of nitrogen in the free space of sample cell 10 at time t. N5 is calculated using equation (9) above. Let N0 denote the amount of nitrogen in the free space of sample cell 10 at the beginning of the desorption measurement. N0 is calculated using equation (9) above using P0 in place of P. Let Nd be the amount of gas desorbed. Nd can be obtained by N6−(N0−N5). Suppose it is measured that T4=298.0 K, T2=298.0 K, T3=77.4 K. The columns of Table 2 indicate some data that may be obtained, and calculated N6, N5 and Nd.

It may happen that the walls of the sample cell may also be covered with condensed gas. In this case, the pressure in sample cell 10 will not decrease until these are removed. In such a case, zero time in a desorption experiment should be taken as the point when the pressure in sample cell 10 begins to decrease, and N6 and (N0−N5) should be adjusted to be zero at this point in time.

TABLE 2

Desorption Data

| Time/s | dP/torr | P/torr | N6/µmol | (N0−N5)/µmol | Nd/µmol |
|---|---|---|---|---|---|
| 0 | 0.0000 | 759.8 | 0.0 | 0.0 | 0.0 |
| 5.0 | 0.130 | 759.7 | 6.845 | 0.163 | 6.682 |
| 10.0 | 0.270 | 759.6 | 14.217 | 0.312 | 13.905 |

Let Ns denote the amount of gas adsorbed at the start of the desorption measurement or the end of the adsorption measurement. A plot of (Ns−Nd) versus P is the desorption isotherm.

We claim:

1. A method for measuring gas amounts adsorbed by a powder sample in a system comprising a supply chamber of predetermined volume, a reference chamber, a temperature and temperature difference measuring means for said supply chamber and reference chamber, a pressure difference measuring means between said supply chamber and reference chamber, a sample cell of predetermined free space and containing a powder sample, a pressure measuring means for said sample cell, and an evacuating means, the method comprising the steps of:
   (a) evacuating said supply chamber said reference chamber, and said sample cell;
   (b) providing said powder sample a surrounding of a substantially constant known temperature;
   (c) isolating said sample cell, said supply chamber, and said reference chamber from said evacuating means and isolating said sample cell from said supply chamber and said reference chamber;
   (d) using a gas supply to supply gas to said supply chamber and said reference chamber, then isolating said supply chamber and said reference chamber from said gas supply by valving means;
   (e) isolating said supply chamber from said reference chamber by valving means, waiting for the pressure to stabilize in both chambers, then measuring the pressure difference and temperature difference between them and the temperatures thereof;
   (f) supplying gas from said supply chamber to said sample cell using a gas flow control means;
   (g) measuring the pressure difference and temperature difference between said reference chamber and said supply chamber and the temperatures thereof, and using said pressure difference, temperature difference, and temperatures, and the volume of said supply chamber, calculating the amount of gas that flowed out from said supply chamber;
   (h) measuring the pressure in said sample cell and using said pressure and the free space and temperature of said sample cell, calculating the amount of gas added to the free space in said sample cell;
   (i) calculating by the arithmetic difference of the gas amounts in steps (g) and (h) the gas amount adsorbed by said powder sample to get the data point of adsorbed amount at this pressure in said sample cell; and
   (j) repeating steps (f) to (i) until the pressure in said sample cell has increased to the required pressure, whereby obtaining data points of adsorbed amount at the increasing pressures in said sample cell.

2. The method of claim 1 for measuring gas amounts adsorbed by a powder sample further including providing accuracies where the measurement errors are less than 0.3% of their measured readings for the measuring of pressure differences and the measuring of pressures.

3. The method of claim 1 for measuring gas amounts adsorbed by a powder sample further including providing for said supply chamber and said reference chamber to be at a substantially equal temperature.

4. The method of claim 1 for measuring gas amounts adsorbed by a powder sample further including providing for the supplying gas to said supply chamber of said step (d) a gas amount such that said supply chamber can supply gas to said sample cell until the pressure therein reaches the pressure required at the end of the adsorption experiment.

5. The method of claim 1 for measuring gas amounts adsorbed by a powder sample wherein the supplying of gas of said step (f) supplies a continuous flow controlled at a rate such that the pressure in said sample cell is in quasi-equilibrium with the adsorbed gas on said powder sample.

6. The method of claim 1 for measuring gas amounts adsorbed by a powder sample, wherein the supplying of gas of said step (f) supplies an intermittent transfer of gas with waiting for pressure equilibrium to be reached in said sample cell after each transfer of gas before proceeding to step (g).

7. An apparatus for measuring gas amounts adsorbed by a powder sample, comprising:
  (a) a supply chamber of predetermined volume;
  (b) a constant pressure reference chamber connected to said supply chamber by conduits and valving means;
  (c) a differential pressure measuring means between said reference chamber and said supply chamber;
  (d) temperature sensors contiguous with said reference chamber and said supply chamber, respectively;
  (e) a sample cell filled with a powder sample and of predetermined free space;
  (f) a gas flow control means with one end connected to said supply chamber and the other end connected to said sample cell;
  (g) a pressure measuring means in communication with said sample cell;
  (h) a constant temperature surrounding that encloses said powder sample;
  (i) evacuating means connected to said supply chamber, said reference chamber, and said sample cell by connecting conduits and valving means; and
  (j) a gas supply connected to said supply chamber and said reference chamber by connecting conduits and valving means.

8. The apparatus of claim 7 wherein said reference chamber is a container of predetermined volume and which is connected to said gas flow control means.

9. The apparatus of claim 7 wherein said differential pressure measuring means and said pressure measuring means are pressure sensors with measurement errors less than 0.3% of the measured readings.

10. The apparatus of claim 7 wherein said gas flow control means is a leak valve.

11. The apparatus of claim 7 wherein said gas flow control means is a shut-off valve.

12. The apparatus of claim 7 wherein said gas flow control means is a mass flow control device.

13. The apparatus of claim 7 wherein said supply chamber and said reference chamber are containers that are thermally contiguous.

14. The apparatus of claim 7 wherein said supply chamber is a container with the gas amount to increase the pressure in said sample cell to the pressure required at the end of the adsorption experiment.

15. The apparatus of claim 7 further including a differential temperature measuring means contiguous with said supply chamber and said reference chamber, respectively.

16. A method for measuring gas amounts adsorbed by a powder sample in a system comprising a supply chamber of predetermined volume, a reference chamber, a temperature measuring means for said supply chamber and reference chamber, a pressure difference measuring means between said supply chamber and reference chamber, a sample cell of predetermined free space and containing a powder sample, a pressure measuring means for said sample cell, and an evacuating means, the method comprising the steps of:

(a) evacuating said supply chamber, said reference chamber, and said sample cell;
  (b) providing said powder sample a surrounding of a substantially constant known temperature;
  (c) isolating said sample cell, said supply chamber, and said reference chamber from said evacuating means and isolating said sample cell from said supply chamber and said reference chamber;
  (d) using a gas supply to supply gas to said supply chamber and said reference chamber, then isolating said supply chamber and said reference chamber from said gas supply by valving means;
  (e) isolating said supply chamber from said reference chamber by valving means, waiting for the pressure to stabilize in both chambers, then measuring the pressure difference between them and the temperatures thereof;
  (f) supplying gas from said supply chamber to said sample cell using a gas flow control means;
  (g) measuring the pressure difference between said reference chamber and said supply chamber and the temperatures thereof, and using said pressure difference and temperatures, and the volume of said supply chamber, calculating the amount of gas that flowed out from said supply chamber;
  (h) measuring the pressure in said sample cell and using said pressure and the free space and temperature of said sample cell, calculating the amount of gas added to the free space in said sample cell;
  (i) calculating by the arithmetic difference of the gas amounts in steps (g) and (h) the gas amount adsorbed by said powder sample to get the data point of adsorbed amount at this pressure in said sample cell;
  (j) repeating steps (f) to (i) until the pressure in said sample cell has increased to the required pressure, whereby obtaining data points of adsorbed amount at the increasing pressures in said sample cell;
  (k) providing for said reference chamber a predetermined volume;
  (l) following step (j), isolating said sample cell from said supply chamber and said reference chamber, and evacuating to vacuum said supply chamber and said reference chamber;
  (m) isolating said reference chamber from said supply chamber and said evacuating means, and continue evacuating said supply chamber;
  (n) supplying gas from said sample cell to said reference chamber using said gas flow control means;
  (o) measuring the pressure and temperature of said reference chamber, and using the pressure, temperature, and volume of said reference chamber, calculating the amount of gas added to said reference chamber;
  (p) measuring the pressure in said sample cell, calculating the change in pressure in said sample cell, and using this pressure change, free space, and temperature of said sample cell, calculating the amount of gas removed from the free space in said sample cell; (q) calculating the arithmetic difference of the gas amounts of steps (o) and (p) to calculate the gas amount desorbed by said powder sample, and subtracting this desorbed amount from the amount adsorbed at the highest pressure in step (j) to get a data point of adsorbed amount at this pressure in said sample cell; and
  (r) repeating steps (n) to (q) until the pressure in said sample cell has fallen to a specified pressure, whereby obtaining said data points of adsorbed amount at the decreasing pressures in said sample cell.

* * * * *